US010784705B2

(12) United States Patent
Scott et al.

(10) Patent No.: US 10,784,705 B2
(45) Date of Patent: Sep. 22, 2020

(54) RECHARGING POWER SOURCES OF IMPLANTABLE MEDICAL DEVICES

(71) Applicant: Medtronic, Inc., Minneapolis, MN (US)

(72) Inventors: Erik R. Scott, Maple Grove, MN (US); David A. Dinsmoor, North Oaks, MN (US); Venkat R. Gaddam, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 203 days.

(21) Appl. No.: 15/965,515

(22) Filed: Apr. 27, 2018

(65) Prior Publication Data

US 2019/0334367 A1   Oct. 31, 2019

(51) Int. Cl.
| | |
|---|---|
| *A61N 1/00* | (2006.01) |
| *H02J 7/02* | (2016.01) |
| *H02J 50/10* | (2016.01) |
| *H02J 50/40* | (2016.01) |
| *A61N 1/36* | (2006.01) |
| *A61N 1/372* | (2006.01) |
| *A61N 1/378* | (2006.01) |
| *H02J 7/00* | (2006.01) |
| *H02J 7/04* | (2006.01) |

(52) U.S. Cl.
CPC .......... *H02J 7/025* (2013.01); *A61N 1/36128* (2013.01); *A61N 1/3787* (2013.01); *A61N 1/37223* (2013.01); *H02J 7/0013* (2013.01); *H02J 7/045* (2013.01); *H02J 50/10* (2016.02); *H02J 50/40* (2016.02)

(58) Field of Classification Search
CPC .......... H02J 7/0013; H02J 50/40; H02J 50/10; A61N 1/3787; A61N 1/37223; A61N 1/36128; A61N 1/3605
See application file for complete search history.

(56) References Cited

U.S. PATENT DOCUMENTS

| | | |
|---|---|---|
| 5,702,431 A | 12/1997 | Wang et al. |
| 6,278,258 B1 | 8/2001 | Echarri et al. |
| 7,167,756 B1 | 1/2007 | Torgerson et al. |
| 8,362,742 B2 | 1/2013 | Kallmyer |
| 9,002,469 B2 | 4/2015 | D'Ambrosio |
| 9,042,995 B2 | 5/2015 | Dinsmoor et al. |
| 2003/0078634 A1 | 4/2003 | Schulman et al. |
| 2008/0172109 A1 | 7/2008 | Rahman et al. |

(Continued)

OTHER PUBLICATIONS

International Search Report and Written Opinion of International Application PCT/US2019/021864, dated Jun. 3, 2019, 11 pp.

*Primary Examiner* — Scott M. Getzow
(74) *Attorney, Agent, or Firm* — Shumaker & Sieffert, P.A.

(57) ABSTRACT

In some examples, a medical device system includes a first implantable medical device. The first implantable medical device (IMD) may comprise circuitry configured to at least one of deliver a therapy to a patient or sense a physiological signal from the patient; generate stimulation deliverable to a patient; a first rechargeable power source; and a secondary coil coupled to the first rechargeable power source, the secondary coil configured to charge the first rechargeable power source via inductive coupling with a primary coil of an external charging device. The medical device system may comprise processing circuitry configured to control charging of the first rechargeable power source based on a charge state of a second rechargeable power source of a second IMD.

28 Claims, 6 Drawing Sheets

(56) References Cited

U.S. PATENT DOCUMENTS

| | | |
|---|---|---|
| 2009/0273318 A1 | 11/2009 | Rondoni et al. |
| 2010/0106223 A1 | 4/2010 | Grevious et al. |
| 2014/0330348 A1 | 11/2014 | Shelton et al. |
| 2015/0054457 A1 | 2/2015 | Kim |
| 2017/0189693 A1 | 7/2017 | Dellamano et al. |

RECHARGING POWER SOURCES OF IMPLANTABLE MEDICAL DEVICES

TECHNICAL FIELD

The disclosure relates to medical devices, and more particularly, to systems and techniques for recharging power sources of one or more implantable medical devices.

BACKGROUND

Implantable medical devices may be used to monitor a patient condition and/or deliver therapy to the patient. In long term or chronic uses, implantable medical devices may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external of the patient, this charging process may be referred to as transcutaneous charging. In some examples, transcutaneous charging may be performed via inductive coupling between a primary coil in the charging device and a secondary coil in the implantable medical device. When a current is applied to the primary coil and the primary coil is aligned to the secondary coil, electrical current is induced in the secondary coil within the patient. Therefore, the external charging device does not need to physically connect with the rechargeable power source for charging to occur.

SUMMARY

This disclosure describes systems, devices, and techniques for recharging power sources of one or more medical devices. When multiple implantable medical devices receive power from an external charging device, at least one of the medical devices and/or the external charging device may manage at least one aspect of the charging process to address differences in charge status between each medical device. In this manner, a power source of a first medical device and a power source of a second medical device can be recharged at the same time.

For example, an external charging device may transcutaneously transmit energy to one or more rechargeable power sources of one or more respective IMDs. The external charging device may query each IMD for a power source charge status and control one or more devices with a higher charge to consume more power prior to charging in order for the IMDs to start charging with similar charge states of the respective power sources. In other examples, an IMD may directly receive communication from another IMD regarding charge state and independently increase power consumption to equalize charge state of the power source to the other IMD prior to charging. In other examples, an IMD may, by independently detecting a full charge state or in response to receiving instruction from an external charging device, stop charging the power source while power continues to be transferred by the external charge device. The IMD may discontinue charging the power source by disconnecting the power source from the secondary coil receiving the power or configuring circuitry to prevent current from flowing in the secondary coil or associated charging circuitry of the IMD.

In one example, this disclosure is directed to a medical system including a first implantable medical device (IMD) comprising stimulation circuitry configured to generate stimulation deliverable to a patient, a first rechargeable power source, and a secondary coil coupled to the first rechargeable power source, the secondary coil configured to charge the first rechargeable power source via inductive coupling with a primary coil of an external charging device, and processing circuitry configured to control charging of the first rechargeable power source based on a charge state of a second rechargeable power source of a second IMD.

In another example, this disclosure is directed to a method for controlling charging of a first rechargeable power source of a first implantable medical device (IMD) in a patient, the method including receiving, at a secondary coil of the first IMD, energy via inductive coupling from a primary coil of an external charging device, controlling, by processing circuitry, charging of the first rechargeable power source based on a charge state of a second rechargeable power source of a second IMD.

In another example, this disclosure is directed to a medical system including a first implantable medical device (IMD) that includes stimulation circuitry configured to generate stimulation deliverable to a patient, a first rechargeable power source; and a secondary coil coupled to the first rechargeable power source, the secondary coil configured to charge the first rechargeable power source via inductive coupling with a primary coil of an external charging device, a second IMD that includes stimulation circuitry configured to generate stimulation deliverable to the patient, a second rechargeable power source, and a secondary coil coupled to the second rechargeable power source, the secondary coil configured to charge the second rechargeable power source via inductive coupling with the primary coil of the external charging device, and processing circuitry configured to determine a charge state of the first rechargeable power source and a charge state of the second rechargeable power source, control the first IMD to achieve a target charge state of the first rechargeable power source based on the charge state of the second rechargeable power source of the second IMD, and control delivering energy from the external charging device to the secondary coils coupled to the first and second rechargeable power sources.

The details of one or more examples are set forth in the accompanying drawings and the description below. Other features, objects, and advantages of examples according to this disclosure will be apparent from the description and drawings, and from the claims.

DETAILED DESCRIPTION

Figure 1:
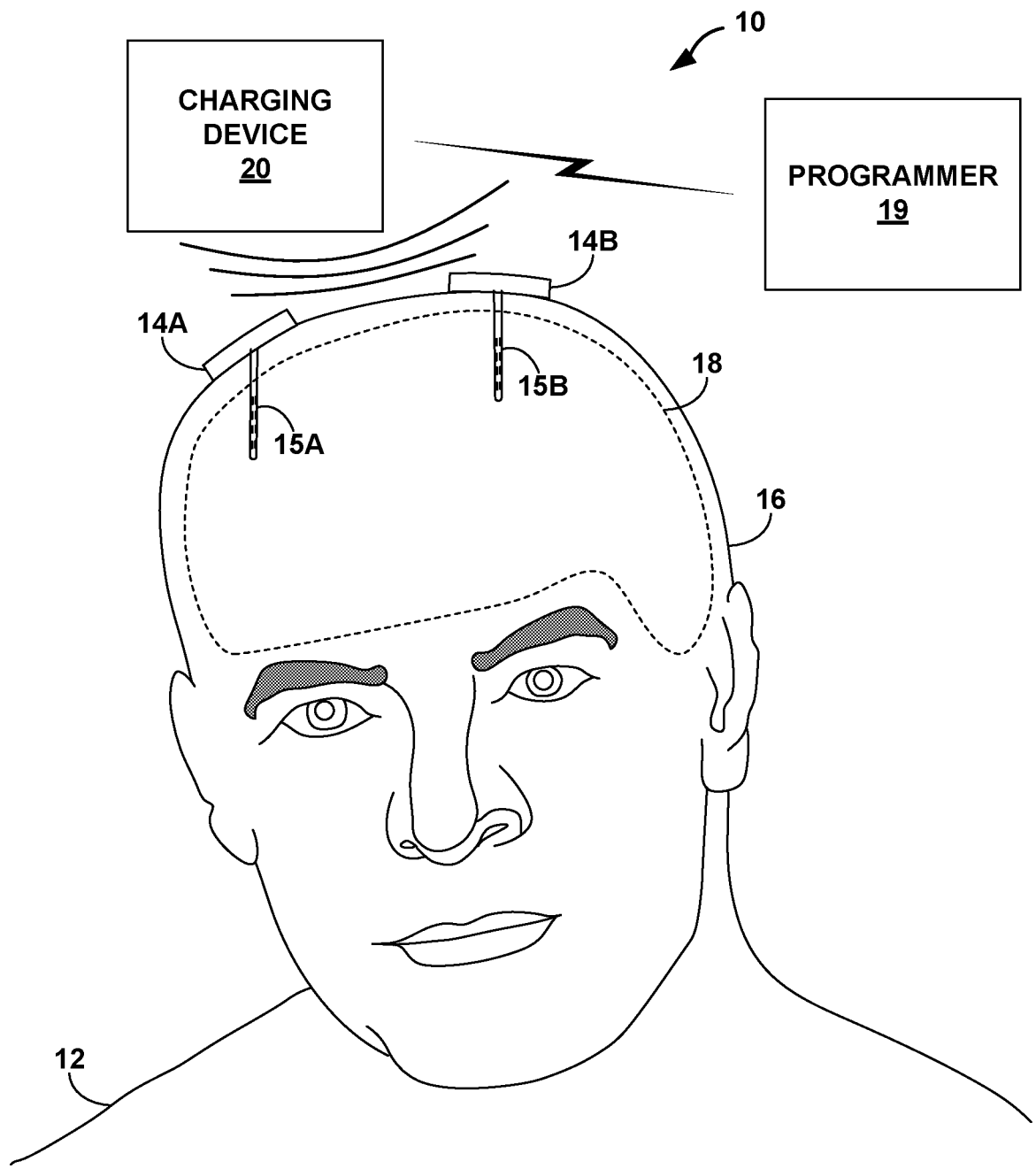
FIG. 1 is a conceptual diagram illustrating an example of a medical system with multiple stimulation leads implanted in the brain of a patient.

This disclosure describes systems (e.g., comprising one or more devices, components, sub-systems, or assemblies) and techniques (e.g., methods or processes) for recharging one or more power sources of one or more respective medical devices. An external charging device is configured to transfer energy to an implantable medical device (IMD), and multiple medical devices may receive this energy to charge respective rechargeable power sources when the medical devices are implanted within range of the external charging device.

An IMD may include a rechargeable power source to extend the operational life of the medical device. The IMD may receive power transcutaneously from an external charge device via a wireless charging scheme, such as inductive coupling. Typically, only a single IMD is positioned within the patient to receive the energy from the external charging device. In some cases, two IMDs may be disposed within the patient, but each IMD may be charged separately when the distance between the IMDs prevents one external charging device from delivering energy to both IMDs at the same time. However, if two or more IMDs are positioned close enough together, or otherwise close enough to the external charging device, the multiple IMDs will receive energy from the external charging device and possibly charge the respective rechargeable power sources at the same time. This scenario may cause a challenge during the charging process. For example, if a first rechargeable power source for a first IMD (e.g., "IMD1") reaches a full charge state prior to a second rechargeable power source from a second IMD (e.g., "IMD2"), the first IMD may need to dispose of the extra charging current as heat and possibly expose surrounding tissue to an undesirable amount of heat. Any example described herein with respect to an "IMD" or "IMD1" may also apply to IMD2 or both of IMD1 and IMD2.

As described herein, one or more devices may operate to reduce temperatures of IMDs during charging and/or provide more efficient recharging when multiple IMDs are inductively coupled to the same external charging device. As discussed above, multiple medical devices (e.g., two IMDs, such as two neurostimulators) may be implanted or disposed externally on a patient in proximity to one another such that both devices receive recharging energy from a common primary coil. When energy is transferred via inductive coupling, for example, the secondary coils would then be inductively coupled to the primary coil of the external charging device. In other words, the magnetic field of the primary coil would induce current in both secondary coils of the respective IMDs. By using the techniques described herein, the external charging device, and the IMDs, may safely charge the respective power sources of multiple devices. For example, these techniques may reduce overheating of the IMDs and thus undesirable heating of tissue around the device. In an example, by using the techniques described herein, multiple power sources of multiple medical devices may be charged more efficiently (e.g., faster) while increasing safety (e.g., better monitor of IMD or tissue temperature) for the patient. An example of the techniques described herein includes controlling charging of a first power source of a first IMD while a second power source of a second IMD approaches a target charge state (e.g., top-off, fully charged, or another desirable or appropriate charge state), while still applying full power from the charging device and preventing overheating of tissue proximate to the first and second IMDs.

In an example, two IMDs may be close enough to each other such that charging energy from the charging device reaches both devices. In other words, recharging circuitry of both IMDs may receive charging energy from the charging device at the same time. In this case, a primary coil of the charging device may couple with two secondary coils of the respective two IMDs. In some instances, each IMD may receive a different amount of the charging energy. Simultaneous charging of multiple IMDs may decrease the amount of time needed to charge all IMDs of a patient, relative to charging each of the multiple IMDs individually and independent of one another. The system may be configured to monitor how each IMD is being charged to manage excess heat, for example. In some examples, one or more of the IMDs may individually manage the charging process to avoid excess charging or heating when multiple IMDs are being charged simultaneously. In other examples, one or more IMDs may receive communications from other IMDs regarding respective charge states of power sources and control charging of the power source based on the charge states of the other IMDs. In other examples, the external charging device may receive information from the IMDs and control charging power and/or transmit instructions to one or more of the IMDs to take action that reduces charge state of one or more power sources, reduces charging rates of one or more power sources, and/or terminates charging of the one or more power sources. In this manner, one or more devices of the system may communicate to coordinate charging between all affected IMDs.

In one example, a medical system includes processing circuitry configured to determine a charge state of a first rechargeable power source of the first IMD (e.g., "IMD1") and/or determine a charge state of a second rechargeable power source of the second IMD (e.g., "IMD2"). IMD1 and IMD2 may be structurally identical or have differing components or different capabilities. IMD1 and IMD2 may be configured to provide the same therapy, different therapies, or even provide different functionalities such as therapy delivery or monitoring services. Although described with respect to IMD1 and IMD2, the systems and techniques may also apply to more than two devices (e.g., three or more medical devices). IMD1 and IMD2 may communicate with each other via communication circuitry in some examples. The communication circuitry may use wireless telemetry to transmit and/or receive information. For example, each IMD may be configured for two-way communication, or in other examples, different IMDs may be configured to only transmit or only receive information. Each IMD in the system may communicate with one or more other devices, such as an external charging device or a programmer device. Any one device or combination of the devices described herein may implement the techniques described herein. In one example, IMD1 may include processing circuitry configured to control charging of one or more devices (e.g., including IMD1). In another example, the external charging device may include processing circuitry configured to control charging of one or more devices.

In general, the processing circuitry may control charging of an IMD prior to or during a recharge session. In this manner, processing circuitry within one or more of the IMDs in the patient, processing circuitry of the external charger, or some combination thereof, may control aspects of delivering charging power to the IMD such as when to charge and at what power levels. Because the charge state of respective power sources for IMD1 and IMD2 may be imbalanced, for example, the processing circuitry may control one or both IMDs to balance the respective charge states prior to or during the recharge session. Balancing charge states of the IMDs may reduce the possibility that one of the IMDs achieves a fully charged state prior to other IMDs. In this disclosure, a charge state of a power source may also be referred to as a charge state of an IMD since each IMD may include a respective power source.

In one example, prior to the recharge session, if IMD1 has a higher charge state than IMD2, then processing circuitry within IMD1, IMD2, and/or the external charging device may control IMD1 to increase its power consumption until the charge state of IMD1 is balanced (e.g., the equivalent, substantially equivalent, or within a tolerance of equivalence) with IMD2. Once the charge states are balanced, the external charging device may start to deliver power to IMD1 and IMD2 during a recharge session. In some examples, the external charger may withhold charging during a recharge session until the charge states of IMD1 and IMD2 are balanced and then start, or continue, charging during the recharge session until each IMD has reached a target charge state. In some examples, an IMD may increase its power consumption by turning on a power consuming feature, where the power consuming feature may not impact therapy or monitoring functionality provided by the IMD. Examples of power consuming features that may be initiated to consume power include turning on wireless telemetry circuitry, executing one or more programs by processing circuitry of the IMD, and/or shunting energy from the power source and through a resistive load. IMD1 may increase its power consumption, and thus reduce the charge state of the power source, in these or other ways. Commands to instruct IMD1 to consume additional power may be transmitted from processing circuitry within IMD1, processing circuitry from another IMD such as IMD2, or processing circuitry within the external charging device. In some examples, control of IMD1 may be shared or distributed between multiple devices.

A system with multiple IMDs receiving recharge power may control charge state of the IMDs using other strategies in addition to, or alternative from, initial power consumption of the IMD with the higher charge state. For example, during a recharge session, if IMD1 will reach, or is expected to reach, a target charge state (e.g., full charge) prior to the target charge state of IMD2, then IMD1 may reduce the amount of recharge current that reaches its power source. In this way, the power source of IMD1 may receive relatively less recharge energy (or none at all) while IMD2 continues to receive recharge energy from the same external charging device. IMD 1 may reduce the amount of recharge energy that reaches the power source of IMD1 for a desired amount of time or until the charge states of the respective power sources of IMD1 and IMD2 are balanced, such as described herein. In one example, IMD1 may reduce the amount of recharge current that reaches its power source by detuning a circuitry of the secondary coil of the IMD1 in which electrical current is induced by the externa charging device. In some examples, detuning the circuitry (e.g., "opening a tuning switch") of a coil is performed as described in U.S. Pat. No. 9,042,995, incorporated herein by reference in its entirety. In another example, IMD1 may disable a self-tuning oscillator of the IMD1 to reduce or prevent electrical current from reaching the power source. In another example, IMD1 may shunt recharge energy through a load (e.g., a resistive load) other than the first power source (e.g., other than the battery) to convert the undesired electrical current into heat instead of stored power in the power source.

In the example of detuning the charging circuitry of the secondary coil, less energy may be transferred from the primary coil in the external charging device to the secondary coil of IMD1. However, this detuning of the charging circuitry may result in less electrical current and lower heat generation as comparted to normal tuning of the charging circuitry that is intended to generate higher electrical current for charging the rechargeable power source. In one example, detuning the charging circuitry of IMD1 may include changing a resonant frequency of a tank circuit, where the tank circuit includes the secondary coil of the IMD1's secondary coil. The charging circuitry may include the tank circuit and other circuits such as rectification and/or filtering circuitry. By detuning and changing the resonant frequency of the tank circuit to be different than the frequency from the external primary coil, lower current may be generated in the secondary coil than would be used for charging the rechargeable power source. In other examples, IMD1 may include a self-tuning oscillator that is coupled across the tank circuit. IMD1 may detune the tank circuit by disabling the self-tuning oscillator, such as switching the self-tuning oscillator out of the tank circuit. In other examples, IMD1 may de-tune a rectifier circuit to de-tune the charging circuitry and reduce the amount of direct current (DC) generated in IMD1 from the alternating current (AC) power provided by the external charging device. For example, IMD1 may switch from full wave rectification to half wave rectification to de-tune the rectifier circuit.

In some examples, the charging device transmits a command that instructs IMD1 to open a circuit coupled to, or is a part of, the secondary coil. In other examples, IMD1 may proactively open a circuit coupled to, or part of, the secondary coil. IMD1 may communicate with charging device 20 to inform charging device 20 that IMD1 has opened the circuit that prevents charging of the IMD1 power source. By creating an open circuit associated with the secondary coil, the energy applied by the external primary coil may not induce a current in the secondary coil. The transmitted command may also instruct that an associated timer be started in response to opening the circuit. For example, the command may instruct IMD1 to open a circuit associated with the secondary coil and start a countdown for IMD1 in which to keep the circuit open. In some examples, the charging device may also track the countdown. Once the countdown of the timer expires, IMD1 may close the circuit and re-enable charging using the secondary coil or the charging device may again request IMD1 to open circuity associated with the secondary coil of IMD1 if the charge state of IMD1 remains greater than the charge state of IMD2. Processing circuitry of the medical system may be configured to control one or more of these steps. In one example, a relay or solid-state switch may be included in the 1 MB to control opening and closing a circuit associated with the secondary coil.

In some examples, the systems and techniques described herein may utilize thermal modeling or monitoring. For example, an IMD may include a temperature sensor that transmits data representative of a temperature to processing circuitry, such as described further below. Processing circuitry of the IMD thus may receive one or more temperature signals from the temperature sensor or from multiple temperature sensors. The processing circuitry may determine a thermal model of the 1 MB and/or surrounding tissue based on the one or more temperature signals. In other examples, the IMD or other device may generate a thermal dosage (e.g., energy delivered over a period of time) delivered to the patient tissue based on the temperature signals and/or known power output by the external charging device. These temperature signals may be generated by one or more temperature sensors of the IMD. In some examples, the processing circuitry may track the temperature of the device or surrounding tissue over time based on the one or more temperature signals, thereby monitoring the thermal state of the IMD and/or tissue surrounding the 1 MB. This thermal modeling or monitoring may enable the IMDs and/or external devices described herein to further reduce the possibility of an implanted device delivering excess heat to a patient. The systems and techniques described herein may enable charging IMDs when multiple IMDs receive power from a single external charging device while avoiding excess charging of one of the IMDs (which may lead to excess heat exposure for surrounding tissue). For example, the charging device may transmit a relatively higher charging power, which may lead to faster charging rates of IMDs, because IMD1 may decouple from the charging energy (e.g., due to a certain charge state or temperature state) while IMD2 remains coupled to continue charging. In this manner, an IMD may determine whether to reduce charge or continue charging based on temperature information and the state of charge of the power source in the IMD. This ability to adjust how and/or when each 1 MB receives power may reduce the need for the external charging device to lower the charging power due to one of the IMDs reaching a full charge state prior to other IMDs receiving power from the same external charging device.

While the description of charging (also referred to as "recharging") an IMD may refer to charging an implantable neurostimulator, the systems and techniques described herein may be used with other types of medical devices or systems. For example, the devices, systems, and techniques described herein may be used with systems including medical devices that deliver electrical stimulation therapy to a patient's heart (e.g., pacemakers, and pacemaker-cardioverter-defibrillators), drug pumps, monitoring devices, or other therapeutic, monitoring, or diagnostic devices.

Although this disclosure generally describes the example of deep brain stimulation, the systems and techniques described herein may be used to deliver other types of electrical stimulation therapy (e.g., spinal cord stimulation, peripheral nerve stimulation, sacral nerve stimulation, pelvic nerve stimulation, gastric nerve stimulation, or vagal nerve stimulation), stimulation of at least one muscle or muscle groups, stimulation of at least one organ such as gastric system stimulation, stimulation concomitant to gene therapy, and, in general, stimulation of any tissue of a patient. In an example, the techniques described herein may be used with any system comprising multiple rechargeable power sources that could be charged from a single, or common, charging device.

FIG. 1 is a conceptual diagram illustrating an example of a medical system 10 that includes multiple stimulation leads 15A and 15B configured to be implanted in the brain 18 of a patient 12. In the example of FIG. 1, medical system 10 includes a charging device 20 configured to deliver energy to one or more implantable medical devices (IMDs) 14A and 14B such as via inductive coupling. For ease of description, IMDs 14A and 14B may be collectively referred to as "IMDs 14." Similarly, for ease of describing two example IMDs, IMD 14A may be referred to as "IMD1," and IMD 14B may be referred to as "IMD2." In an example, IMDs 14 may be at least partially or fully implanted within patient 12. IMDs 14 may include or be coupled to a respective lead (e.g., lead 15A coupled to IMD 14A, and lead 15B coupled to IMD 14B). One or more electrodes of lead 15A and lead 15B are configured to provide electrical signals (e.g., pulses or analog signals) to surrounding anatomical regions of brain 18 in a therapy that may alleviate a condition of patient 12. In some examples, one or both of IMDs 14 may be coupled to more than one lead implanted within brain 18 of patient 12 to stimulate multiple anatomical regions of the brain. In an example, such as shown in FIG. 1, system 10 may include two IMDs 14 that each include a lead. However, more than two IMDs may be disposed in patient 12 in other examples.

Deep brain stimulation (DBS) delivered by one or both of IMDs 14 may treat dysfunctional neuronal activity in the brain which manifests as diseases or disorders such as Huntington's Disease, Parkinson's Disease, or movement disorders. Certain anatomical regions of brain 18 may be responsible for producing the symptoms of such brain disorders. As one example, stimulating an anatomical region, such as the Substantia Nigra, in brain 18 may reduce the number and/or magnitude of tremors experienced by patient 12. Other anatomical regions that may receive stimulation therapy include the subthalamic nucleus, globus pallidus interna, ventral intermediate, and zona inserta. Anatomical regions such as these are targeted by the clinician during pre-operative planning and lead implantation. In other words, the clinician may attempt to position the leads 15A and 15B as close to these regions as possible for DBS therapy.

Typical DBS leads include one or more electrodes placed along the longitudinal axis of the lead, such may be seen on leads 15A and 15B. In one example, each electrode may be a ring electrode that resides along the entire circumference of the lead at one axial location on the lead. Therefore, electrical current from the ring electrodes propagates in all directions from the active electrode. The resulting stimulation field reaches anatomical regions of brain 18 within a certain distance of the lead in all directions.

In other examples, lead 15A or 15B may have a complex electrode array geometry. A complex electrode array geometry include a plurality of electrodes positioned at different axial positions along the longitudinal axis of the lead and a plurality of electrodes positioned at different angular positions around the circumference of the lead (which may be referred to as electrode segments). In some examples, this disclosure may be applicable to leads having all ring electrodes, or one or more ring electrodes in combination with electrode segments at different axial positions and angular positions around the circumference of the lead. In this manner, electrodes may be selected along the longitudinal axis of leads 15A and 15B and along the circumference of the lead. A complex electrode array geometry may allow activating a subset of electrodes of leads 15A and 15B selected to produce customizable stimulation fields that may be directed to a particular side of lead 15A or 15B in order to isolate the stimulation field around the target anatomical region of brain 18.

IMDs 14 may be implanted on cranium 16, such as shown in FIG. 1. IMDs 14 may be positioned elsewhere on cranium 16, such as closer together or further apart than shown in FIG. 1. The precise placement of IMDs 14 may be determined to allow leads 15A and 15B to be implanted at desired locations within the respective hemisphere of brain 18. In an example, IMDs 14 may be positioned at least partially within respective holes or recesses of cranium 16. In an example, IMDs 14 may be implanted elsewhere in the body of patient 12. For example, one or more IMDs 14 may be implanted in the heart of patient 12, or within a thoracic space of patient 12. Regardless of the location of IMDs 14, leads 15A and 15B may be connected to respective IMDs 14A and 14B, and a distal end of each of leads 15A and 15B may be disposed through a burr hole in cranium 16 and implanted within brain 18 to a predetermined location selected to deliver DBS or monitor brain activity.

Medical system 10 may also include multiple leads or electrodes on leads of other shapes and sizes. In some DBS patients, two leads are implanted at symmetrical locations within brain 18 for bilateral stimulation to the respective hemisphere. In particular, a first lead is placed in the right hemisphere of brain 18 and a second lead is placed at the mirrored location within the left hemisphere of the brain. Programmer 19 may receive input from a clinician that defines a desired stimulation field for a first lead, and programmer 19 may generate a mirrored field for the second lead, for example. The clinician may input find adjustments to programmer 19 to finely adjust either stimulation field to accommodate the slight anatomical region differences between the left and right hemispheres of brain 18.

While leads 15A and 15B are described for use in DBS applications throughout this disclosure as an example, leads 15A and 15B, or other leads, may be implanted at any other location within patient 12. For example, leads 15A or 15B may be implanted near the spinal cord, pudendal nerve, sacral nerve, or any other nervous or muscle tissue that may be stimulated, with IMDs also implanted away from cranium 16 in these examples.

Medical system 10 may include external programmer 19, which may be a handheld device, portable computer, or workstation that provides a user interface to a clinician. The user interface may include a display to present information to a user. In general, the user may interact with the user interface. In an example, processing circuitry may provide information (e.g., a signal corresponding to a charge state of one or more power sources) to the user interface. In some examples, the user interface includes a keyboard, keypad, touch screen, mouse, or the like, for receiving input from the user. The user interface may include a light or speaker, such as may be used to provide an indication or alert to the user. For example, if the temperature sensor senses a temperature of the IMD that meets a maximum limit, the processing circuitry described herein may control the user interface, to initiate a blinking light or audible sound to alert the clinician to this or other relevant information.

The clinician may interact with the user interface to program stimulation parameters. The clinician may also interact with the user interface to manually select and program certain electrodes of leads 15A or 15B and adjust the resulting stimulation field with the anatomical regions as guides, or defining one or more stimulation fields only affect anatomical regions of interest. In an example, the clinician may interact with the user interface to determine a charge state of a rechargeable power source of IMDs 14. For example, the charge state may be represented as a percentage or numerical value, visually such as a symbol, or as an alert (e.g., a recharge indication).

Medical system 10 may provide the clinician with additional tools that allow the clinician to program charging device 20, IMD 14A, or IMD 14B. FIG. 1 illustrates a communication link between charging device 20 and programmer 19. The communication link may represent a wired or wireless connection. In some examples, the communication link represents telemetry, as further described herein. Although not shown, any device of medical system 10 may be configured to communicate with any other device of medical system 10. For example, external programmer 19 may be configured to communicate with IMD 14A, IMD 14B, and/or charging device 20. In an example, charging device 20 may be configured to communicate with IMD 14A, IMD 14B, and programmer 19.

In an example, the techniques described herein may be carried out by one or more devices. In one example, the processing circuitry described herein that controls charging of IMDs 14 may be within programmer 19 or within charging device 20. In another example, more than one device in medical system 10 includes processing circuitry configured to carry out the techniques described herein. In another example, IMD 14A includes processing circuitry configured to carry out the techniques described herein. Since two or more devices of medical system 10 may communicate, medical system 10 may leverage multiple devices to perform a portion of the processing and control for charging IMDs 14.

Medical system 10 may include charging device 20 configured to deliver power to each of IMDs 14 for recharging power sources within each IMD. In general, IMDs 14 may each include a power source (e.g., a rechargeable power source). The power source may include a rechargeable battery and/or capacitor. The power source may be coupled to a coil (e.g., a secondary coil), such as via charging circuity. The secondary coil may inductively receive energy from a primary coil 48 (shown in FIG. 3) of charging device 20. Charging device 20 may deliver energy, such as inductively through the skin, or other tissue or anatomical structures, of patient 12 to recharge the power sources of IMDs 14. Charging device 20 may be used to recharge one or more rechargeable power sources of IMDs 14 when implanted in patient 12. Charging device 20 may be a hand-held device, a portable device, or a stationary charging system. In any case, charging device 20 may include components necessary to charge one or more rechargeable power sources through tissue of patient 12. In other examples, charging device 20 include an external programmer (e.g., programmer 19) or other devices configured to perform additional functions. For example, when embodied as an external programmer, charging device 20 may transmit programming commands to IMDs 14 in addition to charge the rechargeable power sources. In another example, charging device 20 may communicate with IMDs 14 to transmit or receive information related to the charging of the rechargeable power sources. For example, IMDs 14A and 14B may transmit temperature information or charge state information of the respective rechargeable power sources. Other information may include information about, for example, charge depletion rates during use, or any other information related to power consumption and recharging of IMDs 14.

Charging device 20 and IMDs 14 may utilize any wireless power transfer techniques that are capable of recharging a rechargeable power source of IMDs 14 when IMDs 14 are implanted within patient 14. In one example, medical system 10 may utilize inductive coupling between a coil of charging device 20 and respective coils of IMD 14A or 14B coupled to the respective rechargeable power source. In inductive coupling, charging device 20 is placed near implanted IMD 14 such that a primary coil of charging device 20 is aligned with (e.g., placed over) a secondary coil of IMD 14A or 14B or both. Charging device 20 may then generate an electrical current in the primary coil based on a selected power level for charging the rechargeable power source. An electrical current in the primary coil creates a magnetic field that, when the primary and secondary coils are aligned, induces an electrical current in the secondary coil within one or both of IMDs 14. The primary coil may generate electromagnetic energy (e.g., radiofrequency (RF) energy) that is received by the secondary coils depending on distance and alignment to the primary coil. Since the secondary coils are associated with and electrically coupled to the rechargeable power sources, the induced electrical current may be used to increase the loaded voltage, or charge level, of the rechargeable power sources. Although inductive coupling is generally described herein, any type of wireless energy transfer may be used to charge one or more rechargeable power sources.

As shown in FIG. 1, IMDs 14 may need to be placed on cranium 16 in locations where each of leads 15 can reach the appropriate target stimulation site within brain 18. However, this may result in IMDs 14 being too close for charging device 20 to only charge one of IMDs 14 at a time. In other words, the electrical field generated by the primary coil of charging device 20 to charge the power source of IMD 14A may also induce at least some electrical current in the secondary coil of IMDs 14B. The benefit to this arrangement is that a single charging device 20 may be used to charge both IMDs 14. However, simultaneous charging of two separate IMDs can present difficulties with appropriate charging rates for each IMD and ceasing energy delivery if one IMD is fully charged but the other IMD still requires more charging. Although IMDs 14 may include mechanisms for diverting surplus electrical current from a fully charged power source to a resistor or other device for dissipation as heat, generating heat in one IMD to remove excess current may result in undesirable temperatures for the patient when the other IMD is also receiving charging energy.

As described herein, system 10 may employ one or more mechanisms for enabling recharge of multiple IMDs with a single charging device. For example, charging device 20 may control a higher power level IMD to reduce the remaining charge in order to create approximately equal charge levels for both of IMDs 14. Therefore, each IMD 14 may be charged fully and reach full charge at approximately the same time. In other examples, an IMD that reaches full charge first may detune or even open circuit charging circuitry in order to reduce or stop the electrical current generated in the secondary coil and delivered to the rechargeable power source. In this manner, the IMD that still requires additional charging may continue to receive charging power without causing excess heat to be generated by the IMD with the already fully charged rechargeable power source.

Figure 2:
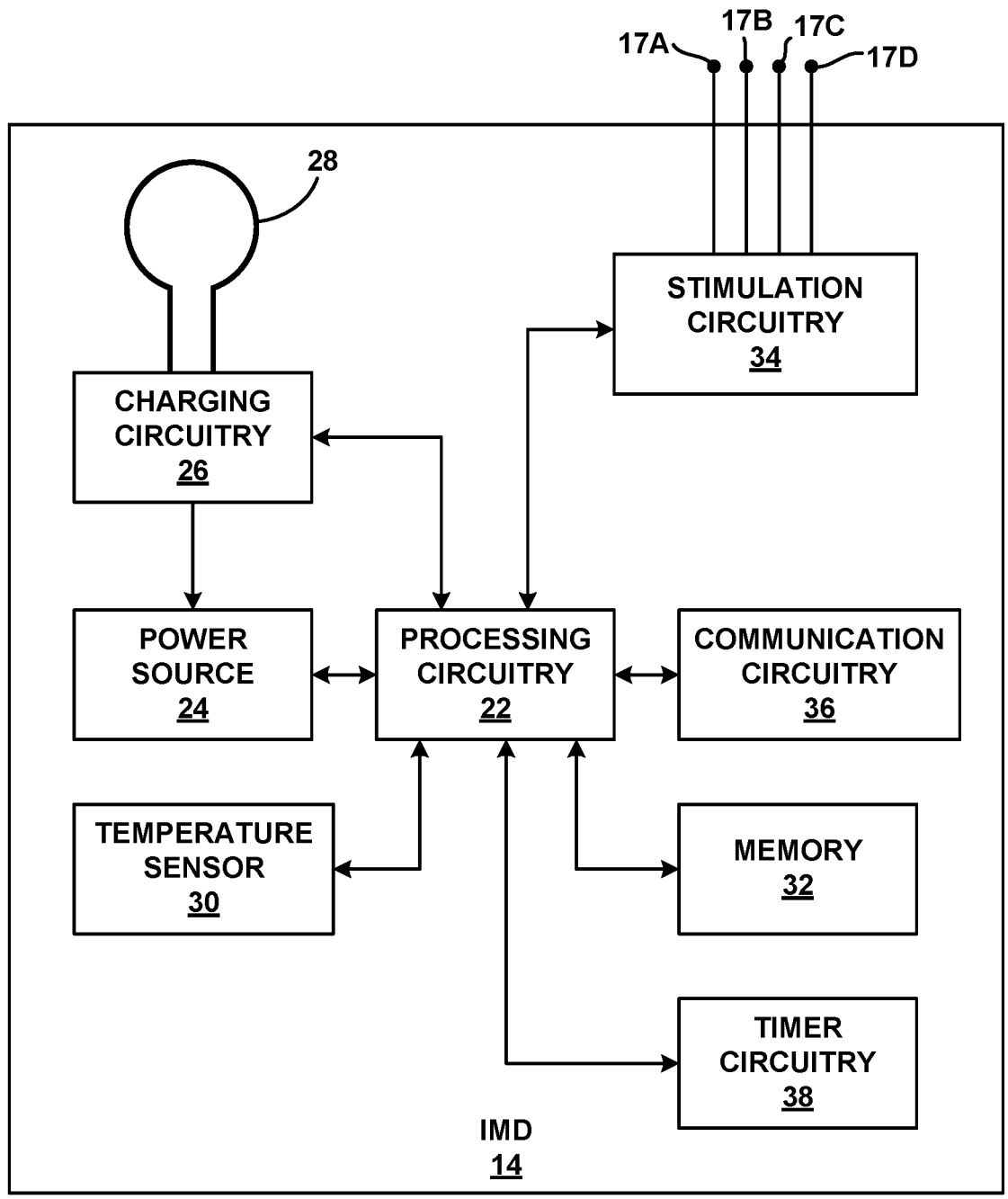
FIG. 2 is a block diagram of the example of the implantable medical device of FIG. 1.

FIG. 2 is a block diagram illustrating example components of an IMD 14. IMD 14 may correspond to IMD 14A, IMD 14B, or another medical device. In the example of FIG. 2, IMD 14 includes processing circuitry 22, power source 24 (e.g., a rechargeable power source), charging circuitry 26, coil 28 (also may be referred to as secondary coil 28), temperature sensor 30, memory 32, stimulation circuitry 34, communication circuitry 36, and timer circuitry 38. In other examples, IMD 14 may include a greater or fewer number of components.

In general, IMD 14 may include any suitable arrangement of hardware, alone or in combination with software and/or firmware, to perform the various techniques described herein attributed to IMD 14 or processing circuitry 22. In various examples, IMD 14 may include one or more processors (e.g., processing circuitry 22), such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors (e.g., processing circuitry) to perform the actions attributed to them. Moreover, although processing circuitry 22, stimulation circuitry 34, charging circuitry 26, and communication circuitry 36 are described as separate, in some examples, processing circuitry 22, stimulation circuitry 34, charging circuitry 26, and communication circuitry 36 are physically and/or functionally integrated. In some examples, processing circuitry 22, stimulation circuitry 34, charging circuitry 26, and communication circuitry 36 correspond to individual hardware units, such as ASICs, DSPs, FPGAs, or other hardware units.

Memory 32 may be configured to store therapy programs or other instructions that specify therapy parameter values for the therapy deliverable by stimulation circuitry 34 and IMD 14. In some examples, memory 32 may also store temperature data from temperature sensor 30, temperature thresholds, instructions for recharging power source 24, circuit models, open-circuit voltage models, tissue models, thresholds, instructions for communication between IMD 14 and programmer 19 or charging device 20, or any other instructions required to perform tasks attributed to IMD 14. In this manner, memory 32 may be configured to store charge states of one or more rechargeable power sources. Processing circuitry 22 may be configured to determine an IMD (e.g., IMD 14) that has a higher or lower charge state than another IMD by comparing two charge states. In response to the comparison, processing circuitry 22 may control charging circuitry 26, for example, of the higher-charged IMD to open a circuit in charging circuitry 26 until processing circuitry 22 determines that both IMDs have similar charge states or are within an appropriate threshold of each other.

Generally, stimulation circuitry 34 may be configured to generate and deliver electrical stimulation under the control of processing circuitry 22. In some examples, processing circuitry 22 controls stimulation circuitry 34 by accessing memory 32 to selectively access and load at least one of the stimulation programs to stimulation circuitry 34. For example, in operation, processing circuitry 22 may access memory 32 to load one of the stimulation programs to stimulation circuitry 34. In such examples, relevant stimulation parameters may include a voltage amplitude, a current amplitude, a pulse rate, a pulse width, a duty cycle, or the combination of electrodes 17A, 17B, 17C, and 17D (or fewer or greater electrodes) that stimulation circuitry 34 uses to deliver the electrical stimulation signal. Although stimulation circuitry 34 may be configured to generate and deliver electrical stimulation therapy via one or more of electrodes 17A, 17B, 17C, and 17D of a lead (e.g., lead 15A or 15B), stimulation circuitry 34 may be configured to provide different therapy to patient 12. For example, stimulation circuitry 34 may be configured to deliver drug delivery therapy via a catheter. These and other therapies may be provided by IMD 14. In this manner, stimulation circuitry 34 may be an example of a therapy module configured to generate and/or deliver a therapy such as electrical stimulation or drug therapy. The therapy module may include a drug pump in the example IMD 14 delivering a drug to patient 12. In some examples, stimulation circuitry 34 may also be configured to sense physiological signals (e.g., electrical signals from the brain such as an electroencephalogram (EEG) or an electrocorticogram (ECoG), electrical signals from other tissues, pressure, temperature, tissue chemistry, and the like) from the brain or any other tissue of patient 12. In some examples, IMD 14 may include sensing circuitry, in addition to stimulation circuitry 34, configured to sense one or more physiological signals from patient 12 and generate an electrical signal representative of the one or more physiological signals.

IMD 14 also includes components configured to receive power from charging device 20 to recharge power source 24, such as when power source 24 has been at least partially depleted. As shown in FIG. 2, IMD 14 includes secondary coil 28 and charging circuitry 26 coupled to power source 24. Charging circuitry 26 may be configured to charge power source 24 with power received from external charging device 20. The power generated by external charging device 20 is, in some examples, generated according to a selected power level determined by either processing circuitry 22 or charging device 20. Although processing circuitry 22 may provide some commands to charging circuitry 26 in some examples, processing circuitry 22 may not need to control any aspect of recharging in other examples.

Secondary coil 28 may include a coil of wire or other device in which an electrical current can be induced via inductive coupling with a primary coil disposed external to patient 12. Although secondary coil 28 is illustrated as a simple loop in FIG. 2, secondary coil 28 may include multiple turns of wire. Secondary coil 28 may include a winding of wire configured such that an electrical current can be induced within secondary coil 28 from a magnetic field generated by the external primary coil. The induced electrical current may then be used by IMD 14 to recharge power source 24. In this manner, an electrical current may be induced in secondary coil 28 associated with power source 24. The induction of electrical current may be caused by a magnetic field generated by electrical current generated in the primary coil of charging device 20 and based on the selected power level. The coupling between secondary coil 28 and the primary coil of charging device 20 may be dependent upon the alignment of the two coils. Generally, the coupling efficiency increases when the two coils share a common axis and are in close proximity to each other.

Although inductive coupling is generally described as the method for recharging power source 24, other wireless energy transfer techniques may additionally or alternatively be used. Any of these techniques may generate heat in IMD 14 that may be monitored, for example, by temperature sensor 30.

Charging circuitry 26 may include one or more circuits that filter and/or transform the electrical signal induced in secondary coil to an electrical signal capable of recharging power source 24. For example, in alternating current induction, charging circuitry 26 may include a half-wave rectifier circuit and/or a full-wave rectifier circuit configured to convert alternating current from the induction to a direct current for power source 24. The full-wave rectifier circuit may be more efficient at converting the induced energy for power source 24. However, a half-wave rectifier circuit may be used to store energy in power source 24 at a slower rate. In some examples, charging circuitry 26 may include both a full-wave rectifier circuit and a half-wave rectifier circuit such that charging circuitry 26 may switch between each circuit to control the charging rate of power source 24 and temperature of IMD 14. As discussed above, charging circuitry 26 may be du-tuned by changing the rectifier circuitry from full-wave to half-wave rectification to reduce the amount of DC power sent to power source 24.

In some examples, charging circuitry 26 may include a tank circuit, which may include secondary coil 28. The tank circuit may be tuned to the external primary coil in order to generate electrical current that charges power source 24. However, in some cases, IMD 14 may include circuitry that is configured to change the resonant frequency of the tank circuit, or tune the tank circuit, as desired. The resonant frequency of the tank circuit may be changed by variable reactance provided by a variable capacitance. For example, IMD 14 may include a tuning switch that receives a control signal from processing circuitry 22 to alter the state and ultimately vary the reactance of the tank circuit that includes secondary coil 28. The tuning switch may open and close to remove or add a capacitor in parallel with a hardwired capacitor, where the hardwired capacitor is in series with secondary coil 28. In this manner the tuning switch may tune the tank circuit for recharge or tune the tank circuit to a resonant frequency other than the recharge frequency to provide power management by reducing the received power during recharge (e.g., detune the tank circuit). Other types of circuitry may also be used by charging circuitry 26 in order to detune coil 28 and change the electrical current generated by coil 28 from the power output by the external primary coil.

In other examples, IMD1 may include a self-tuning oscillator that is coupled across the tank circuit. For example, an oscillator, such as a sinusoidal power amplifier, may be coupled to the tank circuit to drive the tank circuit at a target frequency for inductive coupling with primary coil 48 of charging device 20. Processing circuitry 22 may detune the tank circuit by disabling the self-tuning oscillator, such as switching the self-tuning oscillator out of the tank circuit when less charge current is desired to be induced by secondary coil 28. In some examples, disabling the self-tuning oscillator may not reduce power generating in IMD 1 as much as adding or removing capacitors as discussed above.

In some examples, charging circuitry 26 may include a measurement circuit (e.g., a coulomb counter) configured to measure the current and/or voltage induced in IMD 14 during inductive coupling. This measurement may be used to measure or calculate the power transmitted to power source 24 of IMD 14 from charging device 20. In some examples, charging circuitry 26 or other circuitry may include an electrometer, coulometer or coulomb counter, which may measure the charge current being applied to power source 24 and communicate this charge current to processing circuitry 22. In some examples, processing circuitry 22 may control charging circuitry 26 to open a circuit of charging circuitry 26 to prevent electrical induction and/or detune coil 28 of IMD 14 to generate less power from charging device 20.

Power source 24 may include one or more capacitors, batteries, and/or other energy storage devices. Power source 24 may then deliver operating power to the components of IMD 14. In some examples, power source 24 may include a power generation circuit to produce the operating power. Power source 24 may be configured to operate through hundreds or thousands of discharge and recharge cycles. Power source 24 may also be configured to provide operational power to IMD 14 during the recharge process. In some examples, power source 24 may be constructed with materials to reduce the amount of heat generated during charging. In other examples, IMD 14 may be constructed of materials that may help dissipate generated heat at power source 24, charging circuitry 26, and/or secondary coil 28 over a larger surface area of the housing of IMD 14.

Although power source 24, charging circuitry 26, and secondary coil 28 are shown as contained within the housing of IMD 14, at least one of these components may be disposed outside of the housing. For example, secondary coil 28 may be disposed outside of the housing of IMD 14 to facilitate better coupling between secondary coil 28 and the primary coil of charging device 20. These different configurations of IMD 14 components may allow IMD 14 to be implanted in different anatomical spaces or facilitate better inductive coupling alignment between the primary and secondary coils.

IMD 14 may also include temperature sensor 30. Temperature sensor 30 may include one or more temperature sensors (e.g., thermocouples or thermistors) configured to measure the temperature of 1 MB 14. Temperature sensor 30 may be disposed internal of the housing of 1 MB 14, contacting the housing, formed as a part of the housing, or disposed external of the housing. Temperature sensor 30 positioned within the IMD and may sense an internal temperature of the 1 MB. In an example, temperature sensor 30 may sense a temperature of the housing of the IMD. In other examples, temperature sensor 30 may be positioned on the housing of the IMD and it may sense the temperature of the tissue surrounding the 1 MB. Multiple temperature sensors may be positioned on or within the IMD in some examples.

As described herein, temperature sensor 30 may be used to directly measure the temperature of IMD 14 and/or tissue surrounding and/or contacting the housing of IMD 14. Processing circuitry 22, or charging device 20, may use this temperature measurement as tissue temperature to determine a temperature model of IMD 14 or of the tissue surrounding 1 MB 14. Although a single temperature sensor may be adequate, multiple temperature sensors may provide a better temperature gradient or average temperature of IMD 14. The various temperatures of IMD 14 may also be modeled. Although processing circuitry 22 may continually measure temperature using temperature sensor 30, processing circuitry 22 may conserve energy by only measuring temperature during recharge sessions. Further, temperature may be sampled at a rate to determine adequate temperature measurements or models, but the sampling rate may be reduced to conserve power as appropriate.

Processing circuitry 22 may also control the exchange of information with charging device 20 and/or an external programmer using communication circuitry 36. Communication circuitry 36 may be configured for wireless communication using radio frequency protocols or inductive communication protocols. Communication circuitry 36 may include one or more antennas configured to communicate with charging device 20, for example. Processing circuitry 22 may transmit operational information and receive therapy programs or therapy parameter adjustments via communication circuitry 36. Also, in some examples, IMD 14 may communicate with other implanted devices, such as stimulators, control devices, or sensors, via communication circuitry 36. In addition, communication circuitry 36 may be configured to transmit the measured tissue temperatures from temperature sensor 30, the charge state of power source 24 (e.g., a respective charge state from each of the power sources associated with IMDs 14A and 14B), for example. Communication circuitry of each of IMDs 14A and 14B may communicate information (e.g., power source charge state information) to each other and to other devices, such as programmer 19, charging device 20, or others. In some examples, tissue temperature may be measured adjacent to power source 24.

In other examples, processing circuitry 22 may transmit additional information to charging device 20 related to the operation of power source 24. For example, processing circuitry 22 may use communication circuitry 36 to transmit indications that power source 24 is completely charged, power source 24 is fully discharged, how much charge (e.g., the charge current) is being applied to power source 24, the charge capacity of power source 24, the state-of-charge (SOC) of power source 24, or any other charge information of power source 24. Processing circuitry 22 may also transmit information to charging device 20 that indicates any problems or errors with power source 24 that may prevent power source 24 from providing operational power to the components of IMD 14.

Processing circuity 22 may determine the charge state of power source 24. For example, processing circuitry 22 may include a voltage tester circuit coupled to power source 24 to determine the charge state (e.g., voltage level) of power source 24. In some examples, processing circuitry 22 determines the charge state as a voltage measurement value, as a percentage of full capacity, in relation to another power source charge state (e.g., higher, same, similar, lower), or any combination thereof. In some examples, a user interface (e.g., user interface 54 of FIG. 3) indicates the charge state of one or more power sources. For example, the user interface may display a bar chart, graph, value, a light, or any other indication of charge state of the power source.

In an example, processing circuitry 22 may control timer circuitry 38 to begin a countdown, such as during a recharge session. In an example, processing circuitry 22 may control one or more devices to perform a particular task with a particular duration, such as may be timed via timer circuitry 38. For example, processing circuitry 22 may control charging circuitry 26 to open a circuit for a desired amount of time (e.g., on the scale of seconds, minutes, or hours). Once the countdown expires, processing circuitry 22 may control charging circuitry 26 to close the circuit, such as to tune the IMD to the charging device (e.g., change from a detuned state of the IMD).

Figure 3:
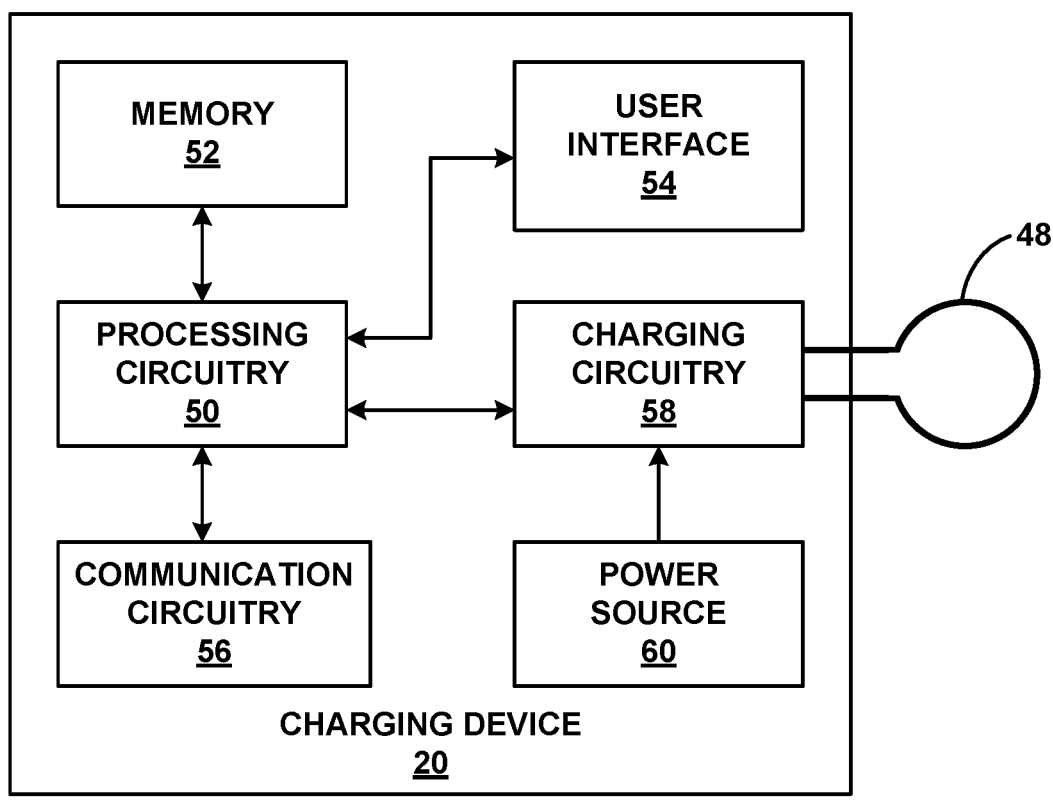
FIG. 3 is a block diagram of the example of the external charging device of FIG. 1.

FIG. 3 is a block diagram of an example of external charging device 20. While charging device 20 may generally be described as a hand-held device, charging device 20 may be a larger portable device or a more stationary device. In addition, in other examples, charging device 20 may be included as part of an external programmer (e.g., programmer 19 shown in FIG. 1) or include functionality of an external programmer. In addition, charging device 20 may be configured to communicate with an external programmer. As illustrated in FIG. 3, charging device 20 may include primary coil 48, processing circuitry 50, memory 52, user interface 54, communication circuitry 56, charging circuitry 58, and power source 60. Memory 52 may store instructions that, when executed by processing circuitry 50, cause processing circuitry 50 and external charging device 20 to provide the functionality ascribed to external charging device 20 throughout this disclosure.

In general, charging device 20 includes any suitable arrangement of hardware, alone or in combination with software and/or firmware, to perform the techniques attributed to charging device 20, and processing circuitry 50, user interface 54, communication circuitry 56, and charging circuitry 58 of charging device 20. In various examples, charging device 20 may include one or more processors (e.g., processing circuitry 50), such as one or more microprocessors, DSPs, ASICs, FPGAs, or any other equivalent integrated or discrete logic circuitry, as well as any combinations of such components. Charging device 20 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processing circuitry 50 and communication circuitry 56 are described as separate, in some examples, processing circuitry 50 and communication circuitry 56 are functionally integrated. In some examples, processing circuitry 50 and communication circuitry 56 and charging circuitry 58 correspond to individual hardware units, such as ASICs, DSPs, FPGAs, or other hardware units.

Memory 52 may store instructions that, when executed by processing circuitry 50, cause processing circuitry 50 and charging device 20 to provide the functionality ascribed to charging device 20 throughout this disclosure. For example, memory 52 may include instructions that cause processing circuitry 50 to control charging circuitry 58, communicate with IMD 14, or instructions for any other functionality. In addition, memory 52 may include a record of selected power levels, calculated estimated energy transfers, or any other data related to charging rechargeable power source 24. Processing circuitry 50 may, when requested, transmit any of this stored data in memory 52 to another computing device for review or further processing.

In some examples, memory 52 may be configured to store measured charge states of one or more power sources of one or more IMDs over time, age of a power source 24, and/or any other factors that may affect voltage of a power source 24. In some examples, memory 52 may be configured to store data representative of an energy absorption tissue model used by processing circuitry 50 to determine the energy absorption of tissue at a particular operating frequency. In some examples, memory 52 may be configured to store data representative of a tissue model used by processing circuitry 50 to calculate tissue temperature based on tissue model and power transmitted to rechargeable power source 24 over a period of time. Tissue model may indicate how temperate of tissue surrounding IMD 14 changes over time.

User interface 54 may include a button or keypad, lights, a speaker that generates audible sounds, a microphone that detects voice commands, a display, such as a liquid crystal (LCD), light-emitting diode (LED), or cathode ray tube (CRT). In some examples the display may be a touch screen. As discussed in this disclosure, processing circuitry 50 may present and receive information relating to the charging of rechargeable power source 24 via user interface 54. For example, user interface 54 may indicate when charging is occurring, quality of the alignment between secondary coil 28 and primary coil 48, the selected power level, current charge level of rechargeable power source 24, duration of the current recharge session, anticipated remaining time of the charging session, or any other information. Processing circuitry 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 24 (e.g., the estimated energy transfer). In this manner, user interface 54 may allow the user to view information related to the charging of rechargeable power source 24 and/or receive charging commands.

Charging device 20 also includes components to transmit power to recharge rechargeable power source 24 associated with IMD 14. As shown in FIG. 3, charging device 20 includes primary coil 48 and charging circuitry 58 coupled to power source 60. Charging circuitry 58 may be configured to generate an electrical current in primary coil 48 from voltage stored in power source 60. Although primary coil 48 is illustrated as a simple loop in the example of FIG. 3, primary coil 48 may include multiple turns of wire. Charging circuitry 58 may generate the electrical current according to a power level selected by processing circuitry 50 based on the estimated energy transfer. As described herein, processing circuitry 50 may select a high power level, low power level, or a variety of different power levels (e.g., three or more different power levels) to control the rate of recharge in rechargeable power source 24. In some examples, the power level may be selected based on the determined temperature of one or more of IMDs 14. In some examples, processing circuitry 50 may control charging circuitry 58 based on a power level selected by processing circuitry 22 of at least one of IMDs 14.

Primary coil 48 may include a coil of wire, e.g., having multiple turns, or other device capable of inductive coupling with a secondary coil 28 disposed within patient 12. Primary coil 48 may include a winding of wire configured such that an electrical current generated within primary coil 48 can produce a magnetic field configured to induce an electrical current within secondary coil 28. Primary coil 48 may be constructed of certain dimensions and/or driven to produce electromagnetic energy of a particular frequency selected for secondary coil 28. The induced electrical current may then be used to recharge rechargeable power source 24. In this manner, the electrical current may be induced in secondary coil 28 associated with rechargeable power source 24. The coupling efficiency between secondary coil 28 and primary coil 48 of charging device 20 may be dependent upon the alignment of the two coils. Generally, the coupling efficiency increases when the two coils share a common axis and are in close proximity to each other. Therefore, if two secondary coils of respective IMDs 14 receive power from a single primary coil 48, one IMD may receive more power than the other IMD. Primary coil 48 may be configured to couple with multiple secondary coils at once. For example, primary coil 48 may be constructed of dimensions to couple with multiple secondary coils of respective multiple IMDs to recharge power sources of the IMDs. User interface 54 of charging device 20 may provide one or more audible tones or visual indications of the alignment.

Charging circuitry 58 may include one or more circuits that generate an electrical signal, and an electrical current, within primary coil 48. Charging circuitry 58 may generate an alternating current of specified amplitude and frequency in some examples. In other examples, charging circuitry 58 may generate a direct current. In any case, charging circuitry 58 may be configured to generate electrical signals that, in turn, causes primary coil 48 to generate a magnetic field that transmits various levels of power to IMD 14. In this manner, charging circuitry 58 may be configured to charge rechargeable power source 24 of IMD 14 with any desirable power level.

A power level may specify a wattage, electrical current in primary coil 48 or secondary coil 28, current amplitude, voltage amplitude, or any other parameter that may be used to modulate the power transmitted from coil 48. The parameters of the power level may be selected based on hardware characteristics of charging device 20 and/or IMD 14.

Power source 60 may deliver operating power to the components of charging device 20. Power source 60 may also deliver the operating power to drive primary coil 48 during the charging process. Power source 60 may include a battery and a power generation circuit to produce the operating power. In some examples, the battery may be rechargeable to allow extended portable operation. In other examples, power source 60 may draw power from a wired voltage source such as a consumer or commercial power outlet.

Although power source 60 and charging circuitry 58 are shown within a housing of charging device 20, and primary coil 48 is shown external to charging device 20, different configurations may also be used. For example, primary coil 48 may also be disposed within the housing of charging device 20. In another example, power source 60, charging circuitry 58, and primary coil 48 may be all located external to the housing of charging device 20 and coupled to charging device 20.

Communication circuitry 56 supports wireless communication between IMD 14, charging device 20, and/or programmer 19 under the control of processing circuitry 50. Communication circuitry 56 may also be configured to communicate with another computing device via wireless communication techniques, or direct communication through a wired connection. In some examples, communication circuitry 56 may be substantially similar to communication circuitry 36 of IMD 14 described herein, providing wireless communication via an RF or proximal inductive medium. In some examples, communication circuitry 56 may include an antenna, which may take on a variety of forms, such as an internal or external antenna. In some examples, communication to IMD 14 may take place via modulation of power from primary coil 48 that is detectable by IMD 14.

Examples of local wireless communication techniques that may be employed to facilitate communication between charging device 20 and IMD 14 include RF communication according to the 802.11 or Bluetooth specification sets or other standard or proprietary telemetry protocols. In this manner, other external devices may be capable of communicating with charging device 20 without needing to establish a secure wireless connection.

Figure 4:
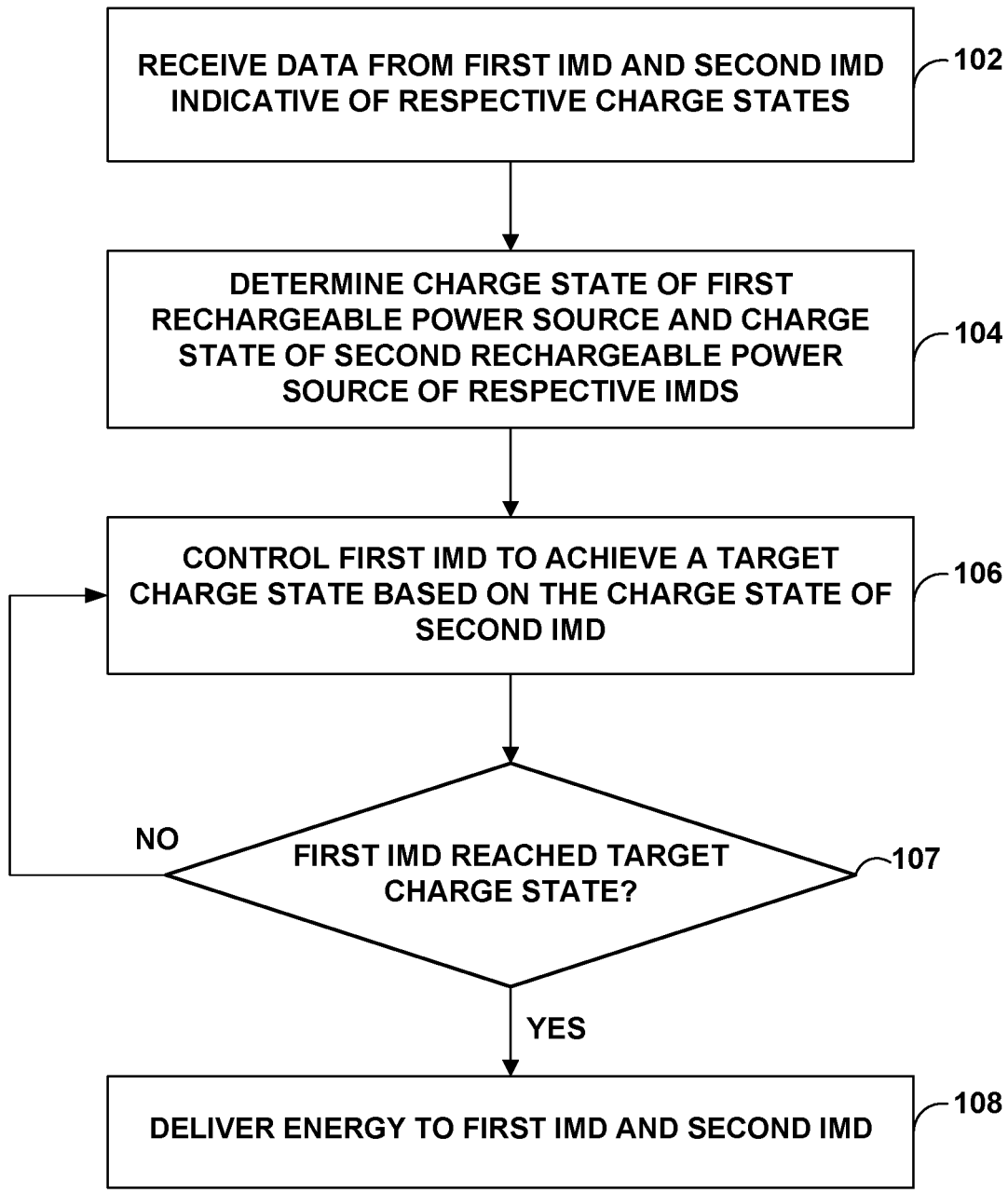
FIG. 4 is a flow diagram that illustrates an example technique for controlling charging of a power source of a medical device by an external charging device.

FIG. 4 is a flow diagram that illustrates an example of a technique for controlling charging of a power source (e.g., power source 24) of a medical device by an external charging device. Processing circuitry 50 of charging device 20 is described as generally performing the technique of example FIG. 4. However, in other examples, the technique of FIG. 4 may be performed by processing circuitry 22 of IMD 14, processing circuitry of another IMD, processing circuitry of external programmer 19, or by any processing circuitry of any single device described herein or any combination thereof. In other words, some functionality may be performed by distributed computing processes. In some examples, one or both of programmer 19 and charging device 20 receive information from IMDs 14. Processing circuitry 50, for example, may control IMD 14A and IMD 14B prior to and during charging. For example, processing circuitry 50 may control IMD 14A to shunt energy through a resistive load prior to a recharging session.

As shown in the example of FIG. 4, processing circuitry 50 of charging device 20 may receive data from first and second IMDs (e.g., IMD1 and IMD2 or IMD 14A and IMD 14B) that is indicative of respective charge states (102). In some examples, communication circuitry 36 of the respective IMD transmits the data indicative of the charge state of each power source 24 to charging device 20. Processing circuitry 50 may then determine the charge state of the first power source of IMD1 and the charge state of the second power source of IMD2 based on information such as the received data (104).

Processing circuitry may control IMD1 to achieve a target charge state based on the charge state of IMD2 (106). In an example, if IMD2 has a charge state less than the charge state of IMD1, then the processing circuitry may control circuitry of IMD1 (e.g., processing circuitry 22 or charging circuitry 26 of IMD1) to achieve the target charge state, such as a charge state similar to the charge state of IMD2. In some examples, the target charge state of IMD1 is within a threshold of the charge state of IMD2 (e.g., within about 5% to about 10% of the charge state of IMD2 or within a threshold voltage value of IMD2). Processing circuitry 50 may transmit a command to IMD1 to perform some action that will achieve the target charge state (e.g., reduce the charge state of power source 24 of IMD1. For example, processing circuitry 50 may transmit a command for IMD1 to turn on a power consuming feature of IMD1, such as powering a communication antenna, powering a sensor, or processing circuitry 22 performing calculations. Typically, these power consuming features are selected so as to not impact therapy delivery or other therapeutic or sensing functions. In some examples, processing circuitry 50 may initiate a telemetry session, run a program on a microprocessor (such as processing circuitry 50), shunt energy through a resistive load, or another task. If processing circuitry 50 determines that IMD1 has not reached the target charge state ("NO" branch of block 107), then processing circuitry 50 continues to control IMD1 to achieve the target charge state (106). If processing circuitry 50 determines that IMD1 has reached the target charge state ("YES" branch of block 107), then charging device 20 may deliver energy to the first and second IMDs (108). In general, before, during, or after the preceding steps, charging device 20 may deliver energy to the first and second IMDs (108).

Figure 5:
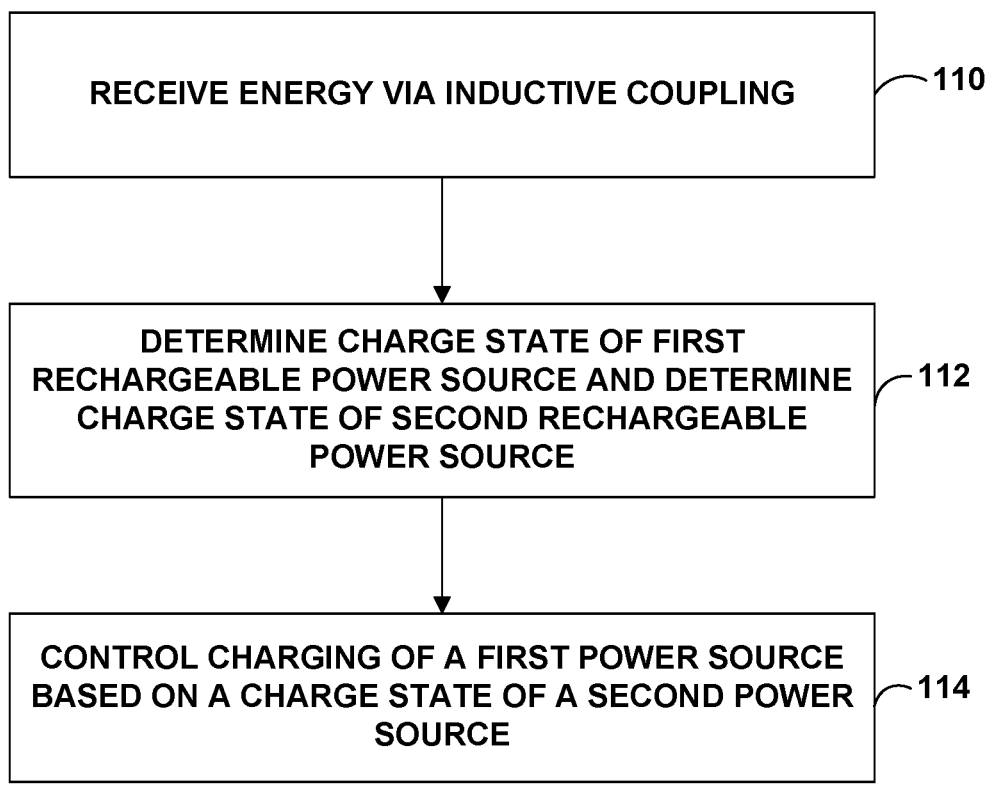
FIG. 5 is a flow diagram that illustrates an example technique for controlling charging of a power source of a medical device by an external charging device.

Charging device 20 may perform the technique of FIG. 5 as part of any recharging of IMDs implanted in patient 12. Alternatively, external programmer 19 may interface between charging device 20 and IMDs 14 in order to relay data and/or commands for one or more of IMDs 14 to send data related to the current charge state of the respective power source 24 and or IMDs 14 to perform an action intended to equalize charge states when multiple IMDs 14 receive power from charging device 20. In some examples, this process may occur prior to the start of charging. In other examples, charge states may be equalized during a charging session as each of IMDs 14 may receive different amounts of power if the primary coil 48 shifts with respect to the different secondary coils of IMDs 14. Charging device 20 may periodically ping each IMD 14 for charge state information and/or each IMD 14 may periodically report charge state during a charging session.

In other examples, IMDs 14 may communicate with each other and/or partially or fully control charge state balancing between IMDs 14. For example, IMD1 may act as a master device that receives charge state data from a slave IMD2, determines which of IMD1 or IMD2 needs to perform a power consuming function to equalize charge state, and transmits a command to IMD2 to perform a function as needed. As shown in the example of FIG. 5, multiple IMDs 14 receive energy via indicative coupling with charging device 20 (110). For example, the primary coil 48 and the secondary coils of the respective IMDs 14 may not necessarily be coupled in the same way. In some situations, charging device 20 may be closer to one of the two or more IMDs. In some situations, primary coil 48 may be oriented to better couple with the secondary coil of one IMD over another. By using the systems and techniques described herein, two or more IMDs may be recharged safely and efficiently regardless of the variable distances between the IMDs and the charging device.

Processing circuitry 22 of IMD1 may determine the charge state of a first rechargeable power source (e.g., the power source of IMD1) and the charge state of a second rechargeable power source (e.g., the power source of IMD2) (112). Processing circuitry 22 of IMD1 may then control charging of the first power source of IMD1 based on the charge state of the second power source of IMD2 (114). For example, during a recharge session, if IMD1 is approaching a target charge state (e.g., full charge) before IMD2, then IMD1 may consume more power to reduce the charge state and/or reduce the amount of recharge current that reaches its own power source, such as described herein. For example, IMD1 may detune its charging circuitry 28 or open a circuit of its secondary coil to reduce the amount of current reaching the power source. Alternatively, IMD1 may directly send a command to IMD2 to reduce the charge state of its power source and/or reduce the power that reaches the power source of IMD2 if IMD2 has a higher charge state than IMD1. IMD1 and IMD2 may communicate directly or via charging device 20 and/or external programmer 19. IMD1 may continue to control IMD1 and/or IMD2 to manage power consumption and/or received charging power based on determined charge state from each IMD (e.g., blocks 112 and 114) during the recharge session from charging device 20.

Figure 6:
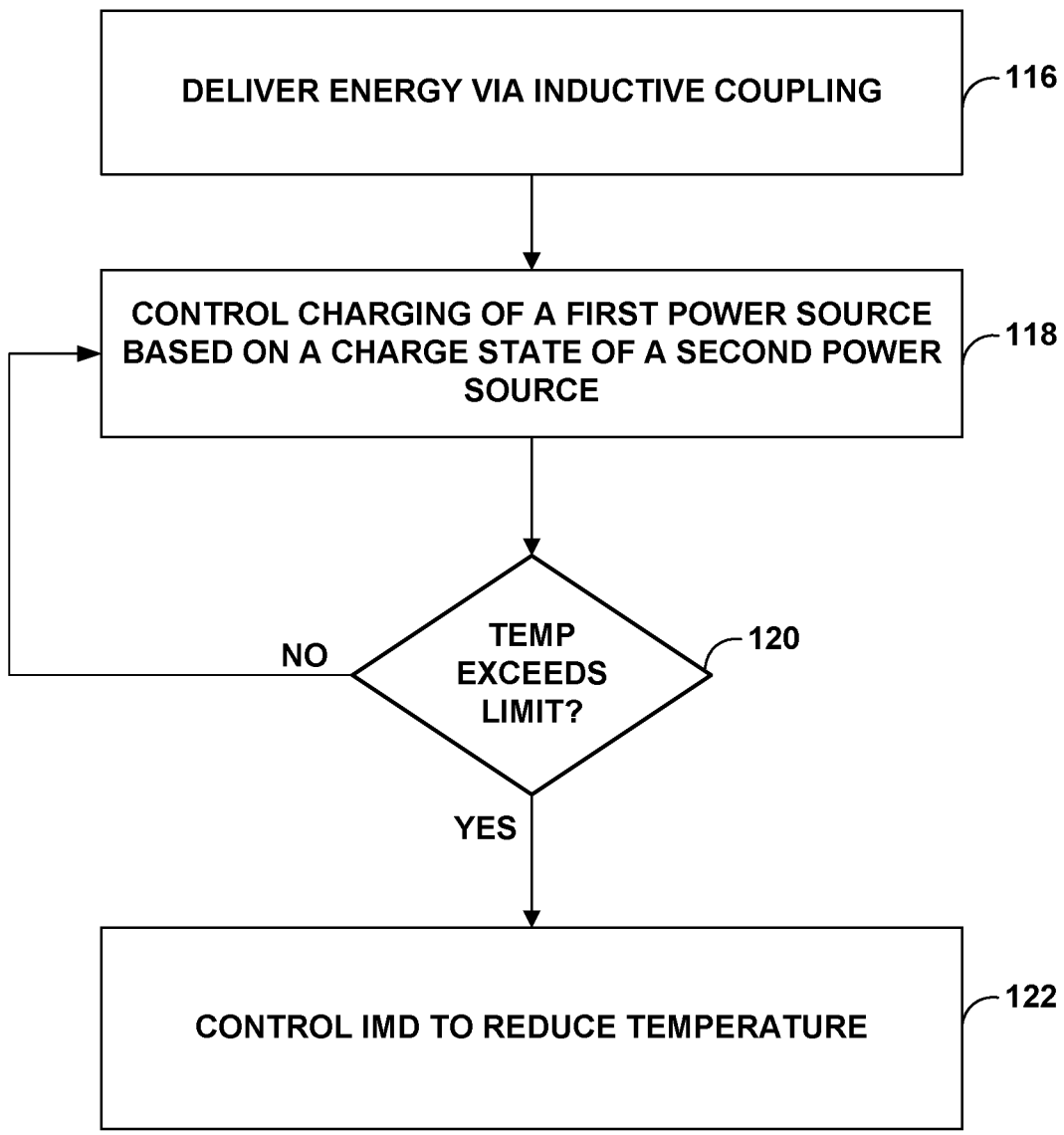
FIG. 6 is a flow diagram that illustrates an example technique for controlling charging of a power source of a medical device by an external charging device.

FIG. 6 is a flow diagram of an example technique for controlling charging of a power source of a medical device (e.g., IMD 14) by an external charging device (e.g., charging device 20) based on temperature of the IMD 14. Processing circuitry 50 of charging device 20 is described in the example of FIG. 6. However, other devices and circuitry, such as processing circuitry 22 of IMDs IMD 14A or 14B, or any combination thereof, may perform the features of FIG. 6.

In the example of FIG. 6, charging device 20 delivers recharge energy to IMDs 14 via indicative coupling (116). As described herein, multiple IMDs 14 may receive recharge energy, and each IMD may be monitored for current charge state of the respective power source and temperate of the respective IMD. Processing circuitry 50 may control charging of power source 24 of IMD1 (e.g., IMD 14A) based on the charge state of the charge state of the power source of IMD2 (e.g., IMD 14B). For example, the power source of IMD2 may not charge as quickly due to inefficient inductive coupling or the charge state of IMD2 is initially lower than the charge state of IMD1.

During the charging session, processing circuitry 50 may determine if a temperature of IMD1 or IMD2 exceeds a maximum limit. IMD1 and IMD2 may periodically transmit the sensed temperature of the respective IMD. If processing circuitry 50 determines that the temperature of either IMD (or patient tissue in other examples) has not reached a maximum temperature limit ("NO" branch of block 120), then processing circuitry 50 continues to deliver energy for charging of both IMDs, such as until both IMDs have reached a target charge state (118). If the temperature of either IMD1 or IMD2 has exceeded the maximum temperature limit ("YES" branch of block 120), then processing circuitry 50 controls the IMD that has exceeded the temperature limit to reduce the temperature of the IMD to an acceptable level while charging device 20 continues to deliver energy via inductive coupling (122). For example, processing circuitry 50 may transmit a command to IMD1 via communication circuitry 56 (or via modulated power delivery from primary coil 48) to perform one or more functions that may reduce the temperature of IMD1. The command may instruct IMD1 to detune circuitry of secondary coil 28 or even open a circuit of secondary coil 28 in order to reduce or eliminate electrical current induced in secondary coil 28. In this manner, charging device 20 may continue to charge IMD2 while also reducing the risk of IMD1 overheating or delivering an undesired temperature to patient 12. In some examples, processing circuitry 50 may control charging within IMD1 and/or IMD2 based on thermal dosage to patient tissue and the state of charge of the power sources of each respective IMD1 and IMD2.

Although charging device 20 is described as performing the features of FIG. 6, processing circuitry of one or more IMDs may perform these features in other examples. For example, processing circuitry of IMD1 may self-monitor the temperature of IMD1 during a charging session and take steps to reduce that temperature in response to detecting the temperature exceeding the temperature limit. In this manner, IMD1 may proactively reduce charging current induced from charging device 20 in situations where the inductive coupling is causing the temperature of IMD1 to exceed the limit. The increase in temperature may be caused by resistive shunting of energy when the power source of IMD1 has reached a full charge state and/or if inductive coupling is generating too much current within IMD1. This could occur due to efficient coupling and/or the patient is covering the IMD during charging such that the IMD is not capable is dissipating heat through patient tissue.

The following numbered examples demonstrate one or more aspects of this disclosure.

Example 1

A medical device system includes: a first implantable medical device (IMD) including: stimulation circuitry configured to generate stimulation deliverable to a patient; a first rechargeable power source; and a secondary coil coupled to the first rechargeable power source, the secondary coil configured to charge the first rechargeable power source via inductive coupling with a primary coil of an external charging device; and processing circuitry configured to control charging of the first rechargeable power source based on a charge state of a second rechargeable power source of a second IMD.

Example 2

In some examples of the medical device system of example 1, the processing circuitry further configured to: identify a start to a charging session; determine that a charge state of the first rechargeable power source is greater than a charge state of the second rechargeable power source; and in response to the determination, control increasing consumption of charge stored by the first rechargeable power source by the first IMD until the charge states of the first and second rechargeable power sources are substantially equivalent.

Example 3

In some examples of the medical device system of examples 1 or 2, the processing circuitry is further configured to: determine that a charge state of the first rechargeable power source is greater than a charge state of the second rechargeable power source; and in response to the determination, control reducing a charging current to the first rechargeable power source.

Example 4

In some examples of the medical device system of example 3, the processing circuitry controls reducing charging current to the first rechargeable power source by at least one of: tuning a rectifier circuit of charging circuitry to a different frequency than a frequency of recharge energy delivered by the external charging device, controlling an oscillator to generate a different frequency than the frequency of recharge energy, or shunting the recharge energy through a resistive load in the first IMD.

Example 5

In some examples of the medical device system of any of examples 1-4, the processing circuitry controls charging of the first rechargeable power source by opening a circuit coupled to the secondary coil of the first IMD to prevent current from being induced in the secondary coil.

Example 6

In some examples of the medical device system of example 5, the medical device system further includes timer circuitry configured to initiate a countdown when the processing circuitry open circuits the secondary coil, and wherein, in response to the end of the countdown, the processing circuitry is configured to close the circuit coupled to the secondary coil.

Example 7

In some examples of the medical device system of any of examples 1-6, the medical device system further includes a temperature sensor coupled to the processing circuitry, wherein the processing circuitry controls charging of the first rechargeable power source based on a temperature of the first IMD, and wherein, in response to the temperature sensor sensing that the temperature of the first IMD meets a maximum temperature limit, the processing circuitry is configured to, at least one of: control decreasing consumption of charge stored by the first rechargeable power source by the first IMD, or close a circuit coupled to the secondary coil of the first IMD.

Example 8

In some examples of the medical device system of any of examples 1-7, the medical device system further includes communication circuitry coupled to the processing circuitry, the communication circuitry configured to receive a first signal corresponding to a charge state of the first rechargeable power source and a second signal corresponding to a charge state of the second rechargeable power source, and wherein the processing circuitry is configured to control charging of the first and second rechargeable power sources based on the first and second signals.

Example 9

In an example, a method for controlling charging of a first rechargeable power source of a first implantable medical device (IMD) in a patient includes: receiving, at a secondary coil of the first IMD, energy via inductive coupling from a primary coil of an external charging device; controlling, by processing circuitry, charging of the first rechargeable power source based on a charge state of a second rechargeable power source of a second IMD.

Example 10

In some examples of the method of example 9, the method further includes: identifying, by the processing circuitry, a charging session; determining, by the processing circuitry, that a charge state of the first rechargeable power source is greater than a charge state of the second rechargeable power source; and in response to the determination, controlling by the processing circuitry, increasing consumption of charge stored by the first rechargeable power source by the first IMD until the charge states of the first and second rechargeable power sources are substantially equivalent.

Example 11

In some examples of the method of example 9 or 10, the method further includes: determining, by the processing circuitry, that a charge state of the first rechargeable power source is greater than a charge state of the second rechargeable power source; and in response to the determination, controlling, by the processing circuitry, reducing a charging current to the first rechargeable power source.

Example 12

In some examples of the method of example 11, controlling reducing a charging current includes at least one of: tuning a rectifier circuit of charging circuitry to a different frequency than a frequency of recharge energy delivered by an external charging device, controlling an oscillator, or shunting the recharge energy through a resistive load in the first IMD.

Example 13

In some examples of the method of any of examples 9-12, the method further includes opening a circuit coupled to the secondary coil of the first IMD to prevent current from being induced in the secondary coil.

Example 14

In some examples of the method of example 13, the method further includes initiating a countdown when the circuit the secondary coil is open circuited, and closing the circuit coupled to the secondary coil in response to the end of the countdown.

Example 15

In some examples of the method of any of examples 9-14, the method further includes: controlling charging of the first rechargeable power source based on a temperature of the first IMD; and in response to the temperature of the first IMD meeting a maximum temperature limit, at least one of: controlling, by the processing circuitry, decreasing consumption of charge stored by the first rechargeable power source by the first IMD, or closing, by the processing circuitry, a circuit coupled to the secondary coil of the first IMD.

Example 16

In some examples of the method of any of examples 9-15, the method further includes receiving, at communication circuitry, a first signal corresponding to a charge state of the first rechargeable power source and a second signal corresponding to a charge state of the second rechargeable power source, and controlling, by the processing circuitry, charging of the first and second rechargeable power sources based on the first and second signals.

Example 17

In an example, a medical system includes: a first implantable medical device (IMD) including: stimulation circuitry configured to generate stimulation deliverable to a patient; a first rechargeable power source; and a secondary coil coupled to the first rechargeable power source, the secondary coil configured to charge the first rechargeable power source via inductive coupling with a primary coil of an external charging device; a second IMD including: stimulation circuitry configured to generate stimulation deliverable to the patient; a second rechargeable power source; and a secondary coil coupled to the second rechargeable power source, the secondary coil configured to charge the second rechargeable power source via inductive coupling with the primary coil of the external charging device; and processing circuitry configured to: determine a charge state of the first rechargeable power source and a charge state of the second rechargeable power source; control the first IMD to achieve a target charge state of the first rechargeable power source based on the charge state of the second rechargeable power source of the second IMD; and control delivering energy from the external charging device to the secondary coils coupled to the first and second rechargeable power sources.

Example 18

In some examples of the medical system of example 17, the processing circuitry is further configured to: identify a start of a charging session; determine that the charge state of the first rechargeable power source is greater than the charge state of the second rechargeable power source; and in response to the determination, control increasing consumption of charge stored by the first rechargeable power source by the first IMD until the charge states of the first and second rechargeable power sources are substantially equivalent.

Example 19

In some examples of the medical system of example 17 or 18, the processing circuitry is further configured to: determine that the charge state of the first rechargeable power source is greater than a charge state of the second rechargeable power source; and in response to the determination, control reducing a charging current to the first rechargeable power source by at least one of: tuning a rectifier circuit of charging circuitry to a different frequency than a frequency of recharge energy delivered by the external charging device, controlling an oscillator to generate a different frequency than the frequency of recharge energy, or shunting the recharge energy through a resistive load.

Example 20

In some examples of the medical system of any of examples 17-19, the processing circuitry is further configured to: open a circuit coupled to the secondary coil of the first IMD to prevent current from being induced in the secondary coil of the first IMD; and the medical system further comprising timer circuitry configured to initiate a countdown when the processing circuitry open circuits the secondary coil of the first IMD, and wherein, in response to the end of the countdown, the processing circuitry is configured to close the circuit coupled to the secondary coil.

Example 21

In an example, a method for controlling charging of a first rechargeable power source of a first implantable medical device (IMD) in a patient includes: determining, by processing circuitry, a charge state of the first rechargeable power source and a charge state of a second rechargeable power source of a second IMD; controlling, by the processing circuitry, the first IMD to achieve a target charge state of the first rechargeable power source based on the charge state of the second rechargeable power source of the second IMD; and delivering, by a primary coil and via inductive coupling, energy to the first and second IMDs.

Example 22

In some examples of the method of example 21, the method further includes: identifying, by the processing circuitry, a start of a charging session; determining, by the processing circuitry, that the charge state of the first rechargeable power source is greater than the charge state of the second rechargeable power source; and in response to the determination, controlling, by the processing circuitry, increasing consumption of charge stored by the first rechargeable power source by the first IMD until the charge states of the first and second rechargeable power sources are substantially equivalent.

Example 23

In some examples of the method of example 21 or 22, the method further includes: determining, by the processing circuitry, that the charge state of the first rechargeable power source is greater than a charge state of the second rechargeable power source; and in response to the determination, controlling, by the processing circuitry, reducing a charging current to the first rechargeable power source by at least one of: tuning a rectifier circuit of charging circuitry to a different frequency than a frequency of recharge energy delivered by an external charging device, controlling an oscillator to generate a different frequency than the frequency of recharge energy, or shunting the recharge energy through a resistive load.

Example 24

In some examples of the method of any of examples 21-23, the method further includes: opening a circuit of a secondary coil of the first IMD to prevent current from being induced in the secondary coil; initiating a countdown, by timer circuitry, when the circuit of the secondary coil is opened, and closing the circuit of the secondary coil in response to the end of the countdown.

Example 25

In some examples, a system includes: means for determining, a charge state of a first rechargeable power source of a first implantable medical device (IMD) and a charge state of a second rechargeable power source of a second IMD; means for controlling the first IMD to achieve a target charge state of the first rechargeable power source based on the charge state of the second rechargeable power source of the second IMD; and means for delivering energy to the first and second IMDs.

Example 26

In some examples, a non-transitory, computer-readable storage medium includes instructions that, when executed, cause one or more processors to: determine a charge state of a first rechargeable power source of a first implantable medical device (IMD) and a charge state of a second rechargeable power source of a second IMD; control the first IMD to achieve a target charge state of the first rechargeable power source based on the charge state of the second rechargeable power source of the second IMD; and deliver energy to the first and second IMDs.

The techniques described in this disclosure, including those attributed to system 10, IMDs 14, charging device 20, and programmer 19, and various constituent components, may be implemented, at least in part, in hardware, software, firmware or any combination thereof. For example, various aspects of the techniques may be implemented within one or more processors or processing circuitry, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques or processes described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), ferroelectric random access memory (FRAM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A medical system comprising:
a first implantable medical device (IMD) comprising:
circuitry configured to at least one of deliver a therapy to a patient or sense a physiological signal from the patient;
a first rechargeable power source; and
a secondary coil coupled to the first rechargeable power source, the secondary coil configured to charge the first rechargeable power source via inductive coupling with a primary coil of an external charging device; and
processing circuitry configured to control charging of the first rechargeable power source based on a charge state of a second rechargeable power source of a second IMD, wherein at least one of the first IMD, the second IMD, the external charging device, or an external programmer comprises the processing circuitry.

2. The medical system of claim 1, wherein the processing circuitry is further configured to:
identify a start to a charging session;
determine that a charge state of the first rechargeable power source is greater than a charge state of the second rechargeable power source; and
in response to the determination, control increasing consumption of charge stored by the first rechargeable power source by the first IMD until the charge states of the first and second rechargeable power sources are substantially equivalent.

3. The medical system of claim 1, wherein the processing circuitry is further configured to:
determine that a charge state of the first rechargeable power source is greater than a charge state of the second rechargeable power source; and
in response to the determination, control reducing a charging current to the first rechargeable power source.

4. The medical system of claim 3, wherein the processing circuitry controls reducing charging current to the first rechargeable power source by at least one of: tuning a rectifier circuit of charging circuitry to a different frequency than a frequency of recharge energy delivered by the external charging device, controlling an oscillator to generate a different frequency than the frequency of recharge energy, or shunting the recharge energy through a resistive load in the first IMD.

5. The medical system of claim 1, wherein the processing circuitry controls charging of the first rechargeable power source by opening a circuit coupled to the secondary coil of the first IMD to prevent current from being induced in the secondary coil.

6. The medical system of claim 5, further comprising timer circuitry configured to initiate a countdown when the processing circuitry open circuits the secondary coil, and wherein, in response to the end of the countdown, the processing circuitry is configured to close the circuit coupled to the secondary coil.

7. The medical system of claim 1, further comprising a temperature sensor coupled to the processing circuitry, wherein the processing circuitry controls charging of the first rechargeable power source based on a temperature of the first IMD, and wherein, in response to the temperature sensor sensing that the temperature of the first IMD meets a maximum temperature limit, the processing circuitry is configured to, at least one of: control decreasing consumption of charge stored by the first rechargeable power source by the first IMD, or close a circuit coupled to the secondary coil of the first IMD.

8. The medical system of claim 1, further comprising communication circuitry coupled to the processing circuitry, the communication circuitry configured to receive a first signal corresponding to a charge state of the first rechargeable power source and a second signal corresponding to a charge state of the second rechargeable power source, and wherein the processing circuitry is configured to control charging of the first and second rechargeable power sources based on the first and second signals.

9. The medical system of claim 1, wherein the first IMD comprises the processing circuitry.

10. The medical system of claim 1, wherein the second IMD comprises the processing circuitry.

11. The medical system of claim 1, wherein the external charging device comprises the processing circuitry.

12. The medical system of claim 1, wherein the external programmer comprises the processing circuitry.

13. A method for controlling charging of a first rechargeable power source of a first implantable medical device (IMD) in a patient, the method comprising:
receiving, at a secondary coil of the first IMD, energy via inductive coupling from a primary coil of an external charging device;
controlling, by processing circuitry, charging of the first rechargeable power source based on a charge state of a second rechargeable power source of a second IMD, wherein at least one of the first IMD, the second IMD, the external charging device, or an external programmer comprises the processing circuitry.

14. The method of claim 13, further comprising:
identifying, by the processing circuitry, a charging session;
determining, by the processing circuitry, that a charge state of the first rechargeable power source is greater than a charge state of the second rechargeable power source; and
in response to the determination, controlling by the processing circuitry, increasing consumption of charge stored by the first rechargeable power source by the first IMD until the charge states of the first and second rechargeable power sources are substantially equivalent.

15. The method of claim 13, further comprising:
determining, by the processing circuitry, that a charge state of the first rechargeable power source is greater than a charge state of the second rechargeable power source; and
in response to the determination, controlling, by the processing circuitry, reducing a charging current to the first rechargeable power source.

16. The method of claim 15, wherein controlling reducing a charging current comprises at least one of: tuning a rectifier circuit of charging circuitry to a different frequency than a frequency of recharge energy delivered by an external charging device, controlling an oscillator, or shunting the recharge energy through a resistive load in the first IMD.

17. The method of claim 13, further comprising opening a circuit coupled to the secondary coil of the first IMD to prevent current from being induced in the secondary coil.

18. The method of claim 17, further comprising initiating a countdown when the circuit the secondary coil is open circuited, and closing the circuit coupled to the secondary coil in response to the end of the countdown.

19. The method of claim 13, further comprising:
controlling charging of the first rechargeable power source based on a temperature of the first 1 MB; and
in response to the temperature of the first 1 MB meeting a maximum temperature limit, at least one of: controlling, by the processing circuitry, decreasing consumption of charge stored by the first rechargeable power source by the first 1 MB, or closing, by the processing circuitry, a circuit coupled to the secondary coil of the first IMD.

20. The method of claim 13, further comprising receiving, at communication circuitry, a first signal corresponding to a charge state of the first rechargeable power source and a second signal corresponding to a charge state of the second rechargeable power source, and controlling, by the processing circuitry, charging of the first and second rechargeable power sources based on the first and second signals.

21. A medical system comprising:
a first implantable medical device (IMD) comprising:
first circuitry configured to at least one of deliver a first therapy to a patient or sense a first physiological signal from the patient;
a first rechargeable power source; and
a secondary coil coupled to the first rechargeable power source, the secondary coil configured to charge the first rechargeable power source via inductive coupling with a primary coil of an external charging device;
a second IMD comprising:
second circuitry configured to at least one of deliver a second therapy to the patient or sense a second physiological signal from the patient;
a second rechargeable power source; and
a secondary coil coupled to the second rechargeable power source, the secondary coil configured to charge the second rechargeable power source via inductive coupling with the primary coil of the external charging device; and
processing circuitry configured to:
determine a charge state of the first rechargeable power source and a charge state of the second rechargeable power source;
control the first IMD to achieve a target charge state of the first rechargeable power source based on the charge state of the second rechargeable power source of the second IMD; and
control delivering energy from the external charging device to the secondary coils coupled to the first and second rechargeable power sources, wherein at least one of the first IMD, the second IMD, the external charging device, or an external programmer comprises the processing circuitry.

22. The medical system of claim 21, wherein the processing circuitry is further configured to:
identify a start of a charging session;
determine that the charge state of the first rechargeable power source is greater than the charge state of the second rechargeable power source; and
in response to the determination, control increasing consumption of charge stored by the first rechargeable power source by the first IMD until the charge states of the first and second rechargeable power sources are substantially equivalent.

23. The medical system of claim 21, wherein the processing circuitry is further configured to:
determine that the charge state of the first rechargeable power source is greater than a charge state of the second rechargeable power source; and
in response to the determination, control reducing a charging current to the first rechargeable power source by at least one of: tuning a rectifier circuit of charging circuitry to a different frequency than a frequency of recharge energy delivered by the external charging device, controlling an oscillator to generate a different frequency than the frequency of recharge energy, or shunting the recharge energy through a resistive load.

24. The medical system of claim 21, wherein the processing circuitry is further configured to:
open a circuit coupled to the secondary coil of the first IMD to prevent current from being induced in the secondary coil of the first IMD; and
the medical system further comprising timer circuitry configured to initiate a countdown when the processing circuitry open circuits the secondary coil of the first IMD, and wherein, in response to the end of the countdown, the processing circuitry is configured to close the circuit coupled to the secondary coil.

25. A method for controlling charging of a first rechargeable power source of a first implantable medical device (IMD) in a patient, the method comprising:
determining, by processing circuitry, a charge state of the first rechargeable power source and a charge state of a second rechargeable power source of a second IMD;
controlling, by the processing circuitry, the first IMD to achieve a target charge state of the first rechargeable power source based on the charge state of the second rechargeable power source of the second IMD; and
delivering, by a primary coil and via inductive coupling, energy to the first and second IMDs.

26. The method of claim 25, further comprising:
identifying, by the processing circuitry, a start of a charging session;
determining, by the processing circuitry, that the charge state of the first rechargeable power source is greater than the charge state of the second rechargeable power source; and
in response to the determination, controlling, by the processing circuitry, increasing consumption of charge stored by the first rechargeable power source by the first IMD until the charge states of the first and second rechargeable power sources are substantially equivalent.

27. The method of claim 25, further comprising:
determining, by the processing circuitry, that the charge state of the first rechargeable power source is greater than a charge state of the second rechargeable power source; and
in response to the determination, controlling, by the processing circuitry, reducing a charging current to the first rechargeable power source by at least one of: tuning a rectifier circuit of charging circuitry to a different frequency than a frequency of recharge energy delivered by an external charging device, controlling an oscillator to generate a different frequency than the frequency of recharge energy, or shunting the recharge energy through a resistive load.

28. The method of claim 25, further comprising:
opening a circuit of a secondary coil of the first IMD to prevent current from being induced in the secondary coil;
initiating a countdown, by timer circuitry, when the circuit of the secondary coil is opened, and closing the circuit of the secondary coil in response to the end of the countdown.

* * * * *